United States Patent
Bogdanovic et al.

(10) Patent No.: US 6,274,774 B1
(45) Date of Patent: *Aug. 14, 2001

(54) PROCESS FOR PREPARING ALDEHYDES IN THE PRESENCE OF AN AQUEOUS PHASE CONTAINING RHODIUM AND SULPHONATED TRIARYLPHOSPHINES AS CATALYST

(75) Inventors: Sandra Bogdanovic, Frankfurt am Main; Carl-Dieter Frohning, Wesel; Helmut Bahrmann, Hamminkeln, all of (DE)

(73) Assignee: Celanese GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/341,396

(22) PCT Filed: Dec. 30, 1997

(86) PCT No.: PCT/EP97/07314

§ 371 Date: Aug. 30, 1999

§ 102(e) Date: Aug. 30, 1999

(87) PCT Pub. No.: WO98/30526

PCT Pub. Date: Jul. 16, 1998

(30) Foreign Application Priority Data

Jan. 13, 1997 (DE) ............................ 197 00 804

(51) Int. Cl.⁷ .................................................. C07C 45/50
(52) U.S. Cl. ........................................ 568/454; 568/451
(58) Field of Search ................... 568/451, 454; 502/24

(56) References Cited

U.S. PATENT DOCUMENTS

| 4,399,312 | * | 8/1983 | Russell et al. | 568/454 |
| 5,091,350 | * | 2/1992 | Cornils et al. | 502/24 |

FOREIGN PATENT DOCUMENTS

| 2627354 | 12/1976 | (DE) . |
| 3135127 | 8/1982 | (DE) . |
| 3412335 | 10/1985 | (DE) . |
| WO9804346 | 2/1998 | (WO) . |

OTHER PUBLICATIONS

Patent Abstract of Japan, 07267890A, Oct. 17, 1995, Toshihiro, et al (1 page).

* cited by examiner

*Primary Examiner*—Sreeni Padmanabhan
(74) *Attorney, Agent, or Firm*—Bierman, Muserlian and Lucas

(57) ABSTRACT

The invention concerns a process for preparing aldehydes by reacting with hydrogen and carbon monoxide at a temperature of between 20 and 170° C. and a pressure of between 1 and 300 bar an olefinically unsaturated $C_6$–$C_{16}$ compound in the presence aqueous phase containing rhodium and sulphonated triarylphosphines as catalyst and between 10 and 70 wt % of a compound of formula (1), $R(OCH_2CH_2)_n OR^1$, R standing for hydrogen, a straight-chain or branched $C_1$–$C_4$ alkyl group or a $C_1$–$C_4$ hydroxyalkyl group, $R^1$ standing for hydrogen or a methyl group, and n standing for an integer from 3 to 50.

38 Claims, No Drawings

PROCESS FOR PREPARING ALDEHYDES IN THE PRESENCE OF AN AQUEOUS PHASE CONTAINING RHODIUM AND SULPHONATED TRIARYLPHOSPHINES AS CATALYST

This is the U.S. National Stage Application of PCT/EP97/07314 filed Dec. 30, 1997.

The present invention relates to a process for preparing aldehydes by reacting olefinic compounds having from 6 to 16 carbon atoms with hydrogen and carbon monoxide at superatmospheric pressure in the presence of an aqueous phase comprising rhodium and sulfonated triarylphosphines as catalyst.

It is known that aldehydes and alcohols can be prepared by reacting olefins with carbon monoxide and hydrogen. The reaction is catalyzed by hydrido-metal carbonyls, preferably those of metals of group VIII of the Periodic Table. Besides cobalt, which is widely used industrially as catalyst metal, rhodium has for some time achieved increasing importance. In contrast to cobalt, rhodium allows the reaction to be carried out at low pressure; in addition, straight-chain n-aldehydes are preferentially formed and iso-aldehydes are formed to only a subordinate extent. Finally, significantly less hydrogenation of the olefins to saturated hydrocarbons occurs when using rhodium catalysts than when using cobalt catalysts.

In the processes which have been introduced in industry, the rhodium catalyst is used in the form of modified hydrido-rhodium carbonyls which contain additional ligands which may, if appropriate, be used in excess. Tertiary phosphines or phosphites have been found to be particularly useful as ligands. Their use makes it possible to reduce the reaction pressure to below 30 MPa.

However, the separation of the reaction products and the recovery of the catalysts homogeneously dissolved in the reaction product create problems in this process. In general, the reaction product is distilled from the reaction mixture. In practice however, owing to the thermal sensitivity of the aldehydes and alcohols formed, this method can only be employed in the hydroformylation of lower olefins, i.e. olefins having up to about 5 carbon atoms in the molecule.

The hydroformylation of long-chain olefins or olefinic compounds containing functional groups forms products having a high boiling point and these cannot be separated from the homogeneously dissolved rhodium complex catalyst by distillation. The thermal stressing of the material being distilled leads to considerable losses of desired products due to thick oil formation and of catalyst due to decomposition of the rhodium complexes.

The separation of the catalyst by thermal means is avoided by use of water-soluble catalyst systems. Such catalysts are described, for example, in DE-C 26 27 354. The solubility of the rhodium complexes is here achieved by use of sulfonated triarylphosphines as constituent of the complex. In this process variant, the catalyst is separated from the reaction product after the hydroformylation reaction is complete simply by separating the aqueous and organic phases, i.e. without distillation and thus without additional thermal process steps. A further feature of this procedure is that n-aldehydes are formed with high selectivity from terminal olefins and iso-aldehydes are formed to only a very subordinate extent. Apart from sulfonated triarylphosphines, carboxylated triarylphosphines are also used as constituents of water-soluble rhodium complexes.

The use of water-soluble catalysts has been found to be useful in the hydroformylation of lower olefins, in particular ethylene and propene. However, if higher olefins such as hexene, octene or decene are used, the reaction rate is greatly reduced. An industrial-scale reaction is no longer economical when using olefins having six or more carbon atoms.

In order to increase the conversion and/or the selectivity of the reaction to n-aldehydes in the hydroformylation of higher olefins by means of water-soluble catalysts, the addition of an amphiphilic reagent (DE 31 35 127 A1) or a solubilizer (DE 34 12 335 A1) has been recommended.

According to both DE 31 35 127 A1 and DE 34 12 335, very high conversions are obtained using quaternary ammonium salts which have a long-chain alkyl radical, while nonionic substances based on polyethylene glycol lead to comparatively low conversions.

As can be seen from Table 7 in DE 31 35 127, the hydroformylation of 1-dodecene by means of rhodium and monosulfonated triphenylphosphine ($3\text{-}Ph_2PC_6H_4SO_3Na$) without addition of an amphiphilic reagent leads to a conversion of 56% (Example 77), while the addition of $C_{12}H_{25}(OCH_2CH_2)_{23}OH$ (="Brij 35") leads to a reduction in the conversion to 37% (Example 78).

According to DE 34 12 335 (Table 4), the hydroformylation of hexene by means of rhodium and trisodium tri(m-sulfophenyl)phosphine without addition of a solubilizer leads to a conversion of 36% (Example 10), while addition of 2.5% of triethylene glycol (Example 14) or 5% of polyglycol 200 (Example 11) gives a conversion of 43.5% or 43% respectively. The addition of the solubilizer results in no significant increase in the conversion, and increasing the amount of solubilizer from 2.5% to 5% also does not increase the conversion. On the other hand, a very high conversion, namely 86%, is achieved with an addition of 2.5% of trimethylhexadecylammonium bromide.

However, the use of quaternary ammonium salts as amphiphilic reagent or solubilizer is not without problems because of the poor biodegradability of these compounds. Thus, the presence of quaternary ammonium salts in wastewater leads to difficulties in wastewater treatment.

Amphiphilic reagents and solubilizers serve to aid mass transfer between the individual phases and thus the miscibility of aqueous catalyst phase and organic phase. An increase in the miscibility of aqueous catalyst phase and organic phase means an increased solubility of the organic phase in the aqueous phase and of the aqueous phase in the organic phase. In this way, increasing amounts of amphiphilic reagent and solubilizer and also rhodium and water-soluble phosphine can get into the organic phase and be carried off with the organic phase after phase separation.

Furthermore, it is to be expected that with increasing miscibility of aqueous catalyst phase and organic phase the demixing required for phase separation will no longer take place to a sufficient extent, if at all, as a result of the formation of emulsions or solutions. A corresponding increase in the miscibility is to be expected particularly when the amount of amphiphilic reagents and solubilizers added is increased.

Increased discharge of rhodium, water-soluble phosphine and amphiphilic reagent or solubilizer via the organic phase is, like reduced demiscibility of the phases, undesirable, since the rhodium, water-soluble phosphine and amphiphilic reagent or solubilizer should remain in the aqueous catalyst phase and good demiscibility is an essential prerequisite for the separation of organic and aqueous phases which is necessary at the end of the hydroformylation.

In view of the above considerations, there is a need for a process which avoids the abovementioned disadvantages and, in addition, can be implemented industrially in a simple manner.

This object is achieved by a process for preparing aldehydes. It comprises reacting an olefinically unsaturated compound having from 6 to 16 carbon atoms with hydrogen and carbon monoxide at from 20 to 170° C. and from 1 to 300 bar in the presence of an aqueous phase comprising rhodium and sulfonated triarylphosphines as catalyst and from 10 to 70% by weight of a compound of the formula (1) $R(OCH_2CH_2)_nOR^1$, where, in the formula (1), R is hydrogen, a straight-chain or branched alkyl radical having from 1 to 4 carbon atoms or a hydroxyalkyl radical having from 1 to 4 carbon atoms, $R^1$ is hydrogen or a methyl radical, in particular hydrogen, and n is an integer from 3 to 50.

In view of the abovementioned findings of DE 34 12 335 (Table 4, Examples 10, 14 and 11) and DE 31 35 127 (Table 7, Examples 77 and 78), it was not to be expected that addition of compounds of the formula (1) $R(OCH_2CH_2)_nOR^1$ in the abovementioned amounts would lead to a significant increase in the conversion and at the same time to a high selectivity in respect of the formation of n-aldehydes.

It is also surprising that the addition of comparatively large to very large amounts of compounds of the formula (1) $R(OCH_2CH_2)_nOR^1$ does not cause a significant increase in the amount of rhodium and sulfonated triarylphosphine in the organic phase and thus to increased discharge of the catalyst via the organic phase.

In addition, it was not to be expected that, despite the comparatively large to very large amounts of compounds of the formula (1), the demiscibility of organic phase and aqueous catalyst phase is high enough to ensure the separation of organic phase and aqueous catalyst phase. Surprisingly, difficult-to-separate emulsions or homogeneous phases or solutions which cannot be separated are not formed.

The aqueous phase comprising the catalyst and the compound of the formula (1) $R(OCH_2CH_2)_nOR^1$ can be prepared in a comparatively simple way by dissolving a water-soluble rhodium salt, the sulfonated triarylphosphines and the compound of the formula (1) in water. Suitable rhodium salts are, without making any claim to completeness: rhodium(III) sulfate, rhodium(III) nitrate, rhodium(III) carboxylates such as rhodium acetate, rhodium propionate, rhodium butyrate and rhodium 2-ethylhexanoate.

The aqueous phase can be used directly in the hydroformylation or subjected beforehand to a preformation of the catalyst under reaction conditions in order to use it subsequently in preformed form.

The olefinic compound used can be an aliphatic olefin, cycloaliphatic olefin or araliphatic olefin having from 6 to 16, in particular from 6 to 10, carbon atoms, preferably an aliphatic α-olefin or cycloaliphatic olefin having from 6 to 12, in particular from 6 to 10, carbon atoms.

The olefinic compound can contain one or more carbon-carbon double bonds. The carbon-carbon double bond can be in a terminal or internal position. Preference is given to olefinic compounds having a terminal carbon-carbon double bond.

Examples of α-olefinic compounds (with a terminal carbon-carbon double bond) are alkenes, alkyl alkenoates, alkenyl alkanoates, alkenyl alkyl ethers and alkenols.

Without claiming completeness, α-olefinic compounds which may be mentioned are 1-hexene, 1-heptene, 1-octene, 1-decene, 1-dodcene, 1-hexadecene, 2-ethyl-1-hexene, styrene, 3-phenyl-1-propene, 1,4-hexadiene, 1,7-octadiene, 3-cyclohexyl-1-butene, hex-1-en-4-ol, oct-1-en-4-ol, 3-butenyl acetate, allyl propionate, allylbutyrate, 4-vinylcyclohexene, n-propyl 7-octenoate, 7-octenoic acid, 5-hexenamide, 1-methoxy-2,7-octadiene and 3-methoxy-1,7-octadiene.

Examples of further suitable olefinic compounds are diisobutylene, tripropylene, octol or dimersol (dimerization products of butenes), tetrapropylene, cyclohexene, dicyclopentadiene, acyclic, cyclic or bicyclic terpenes such as myrcene, limonene and pinene.

For the purposes of the present invention, sulfonated triarylphosphines are phosphines which contain one or two phosphorus atoms, which have three aryl radicals per phosphorus atom, where the aryl radicals are identical or different and are each a phenyl, naphthyl, biphenyl, phenylnaphthyl or binaphthyl radical, in particular a phenyl, biphenyl or binaphthyl radical, and the aryl radicals are connected to the phosphorus atom either directly or via a —$(CH_2)_x$— group, where x is an integer from 1 to 4, in particular from 1 to 2, preferably 1, and which contain at least three —$(SO_3)M$ groups, where M are identical or different and are each H, an alkali metal ion, an ammonium ion, a quaternary ammonium ion, a ½ alkaline earth metal ion or ½ zinc ion, in particular an alkali metal ion, an ammonium ion or a quaternary ammonium ion, preferably an alkali metal ion. The —$SO_3M$ groups are usually located as substituents on the aryl radicals and give the triarylphosphines the required water solubility.

As sulfonated triarylphosphines, preference is given to using compounds of the formula (2)

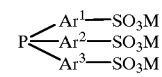

where $Ar^1$, $Ar^2$ and $Ar^3$ are identical or different and are each a phenyl or naphthyl radical, in particular a phenyl radical, and M are identical or different, in particular identical, and are each an alkali metal ion, an ammonium ion, a quaternary ammonium ion or a ½ alkaline earth metal ion or ½ zinc ion, in particular an alkali metal ion or ammonium ion, preferably an alkali metal ion, particularly preferably a sodium ion.

Trisodium tri(m-sulfophenyl)phosphine is particularly suitable as sulfonated triarylphosphine. This trisodium salt of tri(meta-sulfophenyl)phosphine contains, owing to its preparation by sulfonation of triphenylphosphine, amounts of monosulfonated and disulfonated compounds and small amounts of the corresponding phosphine oxides.

Trisodium tri(m-sulfophenyl)phosphine corresponds to the following formula:

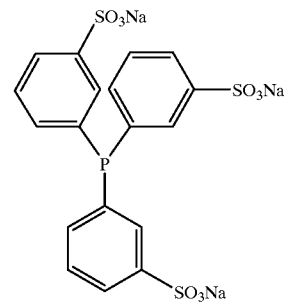

The sulfonated triarylphosphines containing two phosphorus atoms can, for example, contain a radical —$(CH_2)_x$—Ar—Ar—$(CH_2)_x$—, where x is an integer from 1 to 4, in particular from 1 to 2, preferably 1, Ar—Ar is biphenyl or binaphthyl, the —$(CH_2)_x$— group is, via one bond, in each case located in the ortho position to the aryl-aryl bond Ar—Ar connecting the two aryl radicals and is connected via the other bond to a phosphorus atom which in each case bears two further, identical or different aryl radicals, in particular phenyl radicals. These triarylphosphines containing two phosphorus atoms have at least three —$SO_3M$ groups, in particular from 4 to 8 —$SO_3M$ groups, where M is as defined above. The —$SO_3M$ groups are usually located on the aryl radicals of the radical —$(CH_2)_x$—Ar—Ar—$(CH_2)_x$— and on the two further aryl radicals which are connected to the phosphorus.

Examples of such sulfonated triarylphosphines containing two phosphorus atoms are, without making any claim as to completeness, represented by the formulae (3) and (4) below:

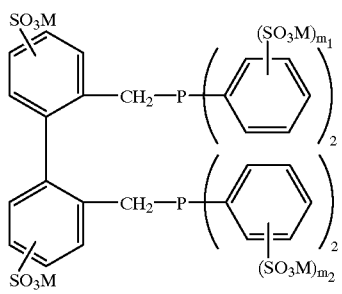
(3)

In (3), $m_1$ and $m_2$ are each, independently of one another, 0 or 1, with the compound of the formula (3) containing from three to six —$SO_3M$ groups.

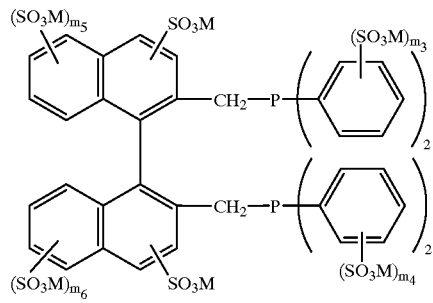
(4)

In (4), $m_3$, $m_4$, $m_5$ and $m_6$ are each, independently of one another, 0 or 1, with the compound of the formula (4) containing from four to eight —$SO_3M$ groups.

Since the compounds (3) and (4) are prepared by sulfonation of the corresponding phosphines of the formulae (3a) and (4a) which contain no —$SO_3M$ groups,

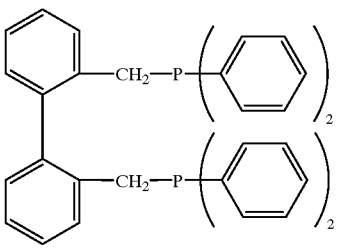
(3a)

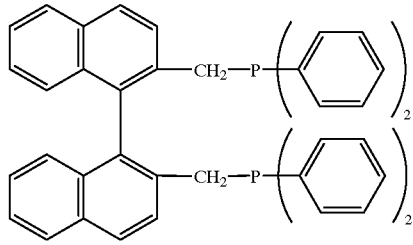
(4a)

they are usually obtained in the form of mixtures of compounds containing different numbers of —$SO_3M$ groups. Thus, a compound of the formula (3) or (4) which contains, for example, three —$SO_3M$ groups also contains compounds having only two —$SO_3M$ groups as well as compounds having four or five —$SO_3M$ groups. A compound of the formula (3) or (4) having, for example, five —$SO_3M$ groups usually also contains compounds having only three or four —$SO_3M$ groups as well as compounds having six or seven —$SO_3M$ groups.

Compounds of the formula (3) have a maximum of six —$SO_3M$ groups, while compounds of the formula (4) have a maximum of eight —$SO_3M$ groups.

For this reason, mixtures of compounds of the formula (3) or (4) having a different number of —$SO_3M$ groups are generally used.

The above-described sulfonated triarylphosphines have, owing to their sulfonate radicals, a solubility in water which is sufficient for carrying out the process.

The aqueous phase comprising rhodium and the compounds of the formula (2) as catalyst and the compound of the formula (1) is usually used in an amount corresponding to from $2 \times 10^{-6}$ to $5 \times 10^{-2}$ mol, in particular from $5 \times 10^{-5}$ to $5 \times 10^{-2}$ mol, preferably from $1 \times 10^{-4}$ to $1 \times 10^{-3}$ mol, of rhodium per mol of olefinic compound.

The amount of rhodium also depends on the type of olefinic compound to be hydroformylated. Although lower catalyst concentrations are possible, in some cases they can prove to be not particulary appropriate, since the reaction rate can be too low and therefore not economical enough. The catalyst concentration can be up to $1 \times 10^{-1}$ mol of rhodium per mol of olefinic compound, but comparatively high rhodium concentrations give no particular advantages.

The aqueous phase comprising rhodium and the trisulfonated triarylphosphine of the formula (2) as catalyst and the compound of the formula (1) $R(OCH_2CH_2)_nOH$ is usually used in a volume ratio to the olefinic compound of from 10:1 to 1:10, in particular from 5:1 to 1:5, preferably from 2:1 to 1:2.

Rhodium and sulfonated triarylphosphines are used in a molar ratio of from 1:5 to 1:2000.

If use is made of a sulfonated triarylphosphine containing one phosphorus atom, for example a compound of the formula (2), rhodium and sulfonated triarylphosphine are usually used in a molar ratio of from 1:10 to 1:1000, in particular from 1:50 to 1:200, preferably from 1:80 to 1:120.

If use is made of a sulfonated triarylphosphine containing two phosphorus atoms, for example a compound of the formula (3) or (4), rhodium and sulfonated triarylphosphine are usually used in a molar ratio of from 1:5 to 1:100, in particular from 1:5 to 1:50, preferably from 1:8 to 1:15.

The aqueous phase contains from 20 to 2000 ppm of rhodium. If a sulfonated triarylphosphine containing one phosphorus atom, for example a compound of the formula (2), is employed, use is in most cases made of an aqueous phase containing from 100 to 1000 ppm, in particular from 200 to 500 ppm, preferably from 300 to 400 ppm, of rhodium.

If a sulfonated triarylphosphine containing two phosphorus atoms, for example compounds of the formula (3) and/or (4), is employed, use is in most cases made of an aqueous phase which contains from 20 to 500 ppm, in particular from 30 to 150 ppm, preferably from 40 to 100 ppm, of rhodium.

The type of oleifinic compound to be reacted can to a certain extent also influence the amount of the compound of the formula (1) $R(OCH_2CH_2)_nOR^1$ to be used.

If the olefinic compound used is an aliphatic α-olefin or a cycloaliphatic olefin containing from 6 to 8 carbon atoms in each case, it has frequently been found to be appropriate to carry out the reaction in the presence of an aqueous phase containing from 10 to 50% by weight, in particular from 20 to 40% by weight, of the compound of the formula (1).

If the olefinic compound is an aliphatic α-olefin or a cycloaliphatic olefin containing from 9 to 12 carbon atoms in each case, it has frequently been found to be appropriate to carry out the reaction in the presence of an aqueous phase containing from 30 to 70% by weight, in particular from 50 to 60% by weight, of the compound of the formula (1).

At this point, it may be mentioned for the sake of completeness that the compounds of the formula (1) $R(OCH_2CH_2)_nOR^1$, where R is hydrogen, a straight-chain or branched alkyl radical having from 1 to 4 carbon atoms or a hydroxyalkyl radical having from 1 to 4 carbon atoms, in particular hydrogen, an alkyl radical having from 1 to 2 carbon atoms or a hydroxyalkyl radical having from 1 to 3 carbon atoms, preferably hydrogen, methyl, hydroxymethyl or hydroxypropyl, and $R^1$ is hydrogen or a methyl radical, in particular hydrogen, are substances which dissolve in water to a sufficient extent.

Attention may be drawn at this point to the following compounds of the formula (1) in which $R^1$ is hydrogen and which are of particular interest.

Without making any claim as to completeness, compounds of the formula $R(OCH_2CH_2)_nOH$ which may be mentioned are polyethylene glycol of the formula $H(OCH_2CH_2)_nOH$ having a mean molecular weight of about 200 (PEG 200), 400 (PEG 400), 600 (PEG 600) or 1000 (PEG 1000), compounds of the formula $CH_3(OCH_2CH_2)_nOH$ having a mean molecular weight of about 350 (M 350), 500 (M 500) or 750 (M 750) or compounds of the formula $CH_3CHOHCH_2(OCH_2CH_2)_nOH$ having a mean molecular weight of about 300 (300 PR), 450 (450 PR), 600 (600 PR) or 1000 (1000 PR), in particular polyethylene glycol having a mean molecular weight of about 400 (PEG 400) and 600 (PEG 600), a compound of the formula $CH_3(OCH_2CH_2)_nOH$ having a mean molecular weight of 500 (M 500) or a compound of the formula $CH_3CHOHCH_2(OCH_2CH_2)_nOH$ having a mean molecular weight of 450 (450 PR) and 600 (600 PR).

For the purposes of the present invention, PEG 200 is a mixture of polyethylene glycols of the formula $H(OCH_2CH_2)_nOH$, where n is an integer from 3 to 6, PEG 400 is a mixture of polyethylene glycols of the formula $H(OCH_2CH_2)_nOH$, where n is an integer from 7 to 10, PEG 600 is a mixture of polyethylene glycols of the formula $H(OCH_2CH_2)_nOH$, where n is an integer from 11 to 16, and PEG 1000 is a mixture of polyethylene glycols of the formula $H(OCH_2CH_2)_nOH$, where n is an integer from 15 to 30. These mixtures can in each case be assigned a corresponding mean molecular weight of about 200 (PEG 200), about 400 (PEG 400), about 600 (PEG 600) or about 1000 (PEG 1000).

For the purposes of the present invention, M 350 is a mixture of compounds of the formula $CH_3(OCH_2CH_2)_nOH$, where n is an integer from 5 to 9, M 500 is a mixture of compounds of the formula $CH_3(OCH_2CH_2)_nOH$, where n is an integer from 9 to 13, and M 750 is a mixture of compounds of the formula $CH_3(OCH_2CH_2)_nOH$, where n is an integer from 12 to 20. These mixtures can in each case be assigned a corresponding mean molecular weight of about 350 (M 350), about 500 (M 500) or about 750 (M 750).

For the purposes of the present invention, 300 PR is a mixture of compounds of the formula $R(OCH_2CH_2)_nOH$, where R is a β-hydroxypropyl radical $CH_3CHOHCH_2$— and n is an integer from 6 to 9, 450 PR is a mixture of compounds of the formula $R(OCH_2CH_2)_nOH$, where R is a β-hydroxypropyl radical $CH_3CHOHCH_2$— and n is an integer from 8 to 14, 600 PR is a mixture of compounds of the formula $R(OCH_2CH_2)_nOH$, where R is a β-hydroxypropyl radical $CH_3CHOHCH_2$— and n is an integer from 12 to 20, and 1000 PR is a mixture of compounds of the formula $R(OCH_2CH_2)_nOH$, where R is a β-hydroxypropyl radical $CH_3CHOHCH_2$— and n is an integer from 18 to 26. These mixtures can in each case be assigned a corresponding mean molecular weight of about 300 (300 PR), about 450 (450 PR), about 600 (600 PR) or about 1000 (1000 PR).

In a number of cases it has been found to be useful to use a polyethylene glycol of the formula $H(OCH_2CH_2)_nOH$, where n is an integer from 3 to 50, in particular from 4 to 30, preferably from 5 to 20, particularly preferably from 6 to 12, as the compound of the formula (1).

It has also been found useful to use a compound (monoether) of the formula $R(OCH_2CH_2)_nOH$, where R is a methyl radical or a β-hydroxypropyl radical and n is an integer from 3 to 50, in particular from 4 to 30, preferably from 5 to 20, as the compound of the formula (1).

It is also possible to use any mixtures of the compounds of the formula (1), namely polyethylene glycols, polyethylene glycol ethers (monoethers) and polyethylene glycol diethers.

The reaction is carried out in the presence of hydrogen and carbon monoxide. The molar ratio of hydrogen to carbon monoxide can be selected within wide limits and is usually from 1:10 to 10:1, in particular from 5:1 to 1:5, preferably from 2:1 to 1:2, particularly preferably from 1.2:1 to 1:1.2. The process is particularly simple if hydrogen and carbon monoxide are used in a molar ratio of 1:1 or approximately 1:1.

In many cases, it is sufficient to carry out the reaction at a temperature of from 50 to 150° C., in particular from 100 to 140° C.

In many cases, it has been found to be useful to carry out the reaction at a pressure of from 10 to 200 bar, in particular from 20 to 150 bar, preferably from 30 to 80 bar.

During the reaction, good mixing of organic phase, aqueous phase and carbon monoxide/hydrogen must be ensured. This can be effected, for example, by intensive stirring and/or pumped circulation of organic and aqueous phases. The organic phase usually comprises the olefinic compound, the aldehydes produced and also small amounts of the aqueous phase, while the aqueous phase usually comprises rhodium, the sulfonated triarylphosphines, the compound of the formula (1), water and small amounts of the organic phase.

At this point, attention may again be drawn to the fact that the reaction conditions, in particular rhodium concentration, pressure and temperature, also depend on the type of olefinic compound to be hydroformylated.

Comparatively reactive olefinic compounds require low rhodium concentrations, low pressures and low temperatures. In contrast, the reaction of relatively less reactive olefinic compounds requires higher rhodium concentrations, higher pressures and higher temperatures.

The process can be carried out particularly successfully if an α-olefinic compound is used. However, other olefinic compounds containing internal carbon-carbon double bonds can also be reacted with good results.

After the reaction is complete, the hydroformylation mixture is freed of carbon monoxide and hydrogen by depressurization and the reaction product, if appropriate after cooling, is separated from the aqueous phase comprising the catalyst and the compound of the formula (1) by phase separation.

The aqueous phase comprising the catalyst and the compound of the formula (1) can be returned to the process of the invention, while the organic phase containing the reaction product is worked up, for example by fractional distillation.

The process can be carried out continuously or batchwise.

The following examples illustrate the invention without restricting it.

Experimental Part

1. Hydroformylation of 1-hexene

EXAMPLE 1a)

(Comparative Experiment to Example 1b) without Addition of Polyethylene Glycol)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS), corresponding to a molar ratio of rhodium to ligand of 1:100, and 21 ml of degassed distilled water and introduced under a stream of nitrogen into a 200 ml steel autoclave. This catalyst solution is heated at 125° C. under 25 bar of synthesis gas pressure ($CO/H_2=1/1$) for 3 hours while stirring, with the solution acquiring a yellow color.

II Hydroformylation 30 ml (240 mmol) of 1-hexene are added to the preformed catalyst solution from I at a reaction pressure of 30 bar and at 125° C. via an upstream 200 ml steel autoclave using slight overpressure. The ratio of olefin to rhodium is 1039:1. The hydroformylation reaction is started by switching on the magnetic stirrer. During a reaction time of 3 hours, the temperature is held at 125° C. and the reaction pressure is kept constant within a pressure band of ±2 bar by manual addition of synthesis gas. After 3 hours have elapsed, stirring and heating are switched off, the autoclave is cooled to from 40 to 50° C. and the upper product phase is separated from the catalyst phase in a separating funnel. Product phase and catalyst phase are weighed. The composition of the product phase is determined by means of gas chromatography and $^1$H-NMR spectroscopy, and the yield of hydroformylation products and the ratio of n- to iso-heptanal are determined from the composition. The rhodium content of the organic phase is, after digestion of the sample, determined by elemental analysis using graphite-furnace atomic absorption spectrometry. The yield of hydroformylation products is 31.2% and the n/iso ratio is 98:2. The organic phase contains <0.05 ppm of Rh. (Example 1a) in Table 1).

EXAMPLE 1b)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS) and added while stirring to 21 ml of degassed polyethylene glycol 400 (PEG 400) (warming!). The catalyst phase is introduced under a stream of nitrogen into a 200 ml steel autoclave and is heated at 125° C. under 25 bar synthesis gas pressure ($CO/H_2=1/1$) for 3 hours while stirring.

II Hydroformylation

Using a method similar to Example 1a), 30 ml (240 mmol) of 1-hexene are added to the preformed catalyst solution from I. The hydroformylation is carried out using a method similar to Example 1a) at 125° C. and 30 bar of synthesis gas. The composition of the product phase is determined by means of gas chromatography and $^1$H-NMR spectroscopy, and the conversion and the selectivity are determined from the composition. The noble metal loss into the organic phase is determined. The yield of hydroformylation product is 82.6% and the n/iso ratio is 94:6. The organic phase contains <0.5 ppm of Rh. (Example 1b) in Table 1).

EXAMPLE 1c)

(Comparative Experiment to Example 1d) without Addition of Polyethylene Glycol)

The procedure of Example 1a) is repeated, except that a reaction pressure of 50 bar is employed in the hydroformylation reaction. After a reaction time of 3 hours, the product phase is separated off and analyzed as described above. The yield of hydroformylation products is 39.2% and the n/iso ratio is 97:3. The organic phase contains <0.03 ppm of Rh. (Example 1c) in Table 1).

EXAMPLE 1d)

The procedure of Example 1b) is repeated, i.e. the catalyst phase is composed of 60 mg of rhodium(III) acetate, 39 ml of a 0.6 M solution of trisodium tri(m-sulfophenyl) phosphine (Na-TPPTS) and 21 ml of degassed polyethylene glycol 400 (PEG 400). The preformation conditions are identical. However, a reaction pressure of 50 bar is employed in the hydroformylation reaction. After a reaction time of 3 hours, the product phase is separated and analyzed as described above. The yield of hydroformylation products is 94.7% and the n/iso ratio is 89:11. The organic phase contains 0.08 ppm of Rh. (Example 1d) in Table 1).

EXAMPLE 1e)

(Comparative Experiment to Example 1f) without Addition of Polyethylene Glycol)

The procedure of Example 1a) is repeated, except that a reaction pressure of 80 bar is employed in the hydroformylation reaction. After a reaction time of 3 hours, the product phase is separated off and analyzed as described above. The yield of hydroformylation products is 36.2% and the n/iso ratio is 96:4. The organic phase contains <0.5 ppm of Rh. (Example 1e) in Table 1).

EXAMPLE 1f)

The procedure of Example 1b) is repeated, i.e. the catalyst phase is made up from 60 mg of rhodium(III) acetate, 39 ml of a 0.6 M aqueous solution of trisodium tri(m-sulfophenyl) phosphine (Na-TPPTS) and 21 ml of degassed polyethylene glycol 400 (PEG 400) and is preformed under the above-described conditions. However, a reaction pressure of 80 bar is employed in the hydroformylation reaction. After a reaction time of 3 hours, the product phase is separated off and analyzed as described above. The yield of hydroformylation products is 93.5% and the n/iso ratio is 79:21. The organic phase contains 0.39 ppm of Rh. (Example 1f) in Table 1).

EXAMPLES 1g) to 1p)

The further Examples 1g)–1p) of the two-phase hydroformylation of 1-hexane are carried out by a similar method.

The amount specified in Table 1 of a polyethylene glycol 200, 400 or 600 (PEG 200, PEG 400 or PEG 600) or alkyl ethoxylate (Genapol T 250: polyethylene glycol tetradecyl ether containing 26 ethoxy units) is added to a solution of 60 mg of rhodium(III) acetate in 39 ml of a 0.6M aqueous solution of trisodium tri(m-sulfophenyl)phosphine (Na-TPPTS), the solution is made up to a total volume of 60 ml with degassed, distilled water and is preformed by a method similar to Example 1a). After addition of 30 ml of 1-hexene as described in Example 1a), the hydroformylation reaction is carried out at the reaction pressure indicated in Table 1. The reaction conditions, the yield of hydroformylation products and the other analytical data as well as the rhodium content of the organic phase are summarized in Table 1.

surfactants, are not suitable for the two-phase hydroformylation carried out.) The reaction conditions and the analytical data for Examples 1a) to 1p) are summarized in the following table.

TABLE 1

Hydroformylation of 1-hexene
Constant conditions: T = 125° C., 240 mmol of olefin, total volume of catalyst phase = 60 ml,
weight of rhodium(III) acetate used = 60 mg; Na-TPPTS/Rh ratio = 100/1; olefin/Rh ratio = 1039/1

| Example | 1-Hexene [mmol] | Additive Type | Amount [ml] | % by weight[1] | Pressure [bar] | Reaction time [min] | Yield [%] | n/iso[2] | Rh[ppm][3] |
|---|---|---|---|---|---|---|---|---|---|
| 1a) | 240 | — | — | — | 30 | 180 | 31.2 | 98:2 | <0.05 |
| 1b) | 240 | PEG 400 | 21 | 35 | 30 | 180 | 82.6 | 94:6 | <0.5 |
| 1c) | 240 | — | — | — | 50 | 180 | 39.2 | 97:3 | n.d. |
| 1d) | 240 | PEG 400 | 21 | 35 | 50 | 180 | 94.7 | 89:11 | 0.08 |
| 1e) | 240 | — | — | — | 80 | 180 | 36.2 | 96:4 | <0.5 |
| 1f) | 240 | PEG 400 | 21 | 35 | 80 | 180 | 93.5 | 79:21 | 0.39 |
| 1g) | 240 | PEG 400 | 9 | 16 | 50 | 180 | 70.9 | 95:5 | 0.05 |
| 1h) | 240 | PEG 400 | 12 | 21 | 50 | 180 | 80.0 | 93:7 | 0.19 |
| 1j) | 240 | PEG 400 | 15 | 26 | 50 | 180 | 91.2 | 93:7 | 1.4 |
| 1l) | 240 | PEG 400 | 18 | 30 | 50 | 180 | 92.3 | 91:9 | 0.44 |
| 1m) | 240 | PEG 400 | 21 | 35 | 50 | 180 | 94.2 | 91:9 | 0.29 |
| 1n) | 240 | PEG 200[4] | 9 | 16 | 50 | 180 | 79.5 | 95:5 | 0.1 |
| 1o) | 240 | PEG 600[6] | 9 | 16 | 50 | 180 | 78.1 | 94:6 | 0.3 |
| 1p) | 240 | Genapol[7] | 9 | 16 | 50 | 180 | n.d. | n.d. | n.d.[8] |

[1]% by weight of additive based on the catalyst phase
[2]Ratio of n-heptanal to 2-melhylhexanal (iso-heptanal)
[3]Rhodium content of the organic phase
[4]PEG 200 = H(OCH$_2$CH$_2$)$_n$OH; n = 5 to 7; [5]PEG 400 = H(OCH$_2$CH$_2$)$_n$OH; n = 7 to 10; [6]PEG 600 = H(OCH$_2$CH$_2$)$_n$OH; n = 11 to
[7]Genapol T 250 = C$_{12}$H$_{25}$(OCH$_2$CH$_2$)$_n$OH; n = 26
[8]No phase separation takes place.
n.d. = not determined or, in Example 1p), not determinable

EXAMPLE 1p)

(Comparative Experiment to Examples 1g), 1n) and 1o) without Addition of Polyethylene Glycol)

In Example 1p), Genapol T 250® C$_{12}$H$_{25}$(OCH$_2$CH$_2$)$_{26}$OH, an alcohol ethoxylate containing 26 ethoxylate units and an alkyl chain having 12 carbon atoms, is used as additive in place of polyethylene glycol 200, 400 or 600 and the catalyst solution is preformed in the usual manner. After addition of 30 ml (240 mmol) of 1-hexene, the hydroformylation is carried out as described in Example 1c). When the reaction is complete, a dark brown solution is obtained and this does not, as would have been expected from DE 31 35 127, separate into an organic phase and a polar catalyst phase. Cooling gives a pale yellow, viscous reaction mass in which no product phase forms even after 24 hours. It is not possible to analyze the reaction product by gas chromatography. From the consumption of synthesis gas, the conversion is calculated as about 45%. (As Example 1p) demonstrates, alcohol ethoxylates having relatively long alkyl chains, as are used commercially as nonionic 2. Hydroformylation of 1-octene

EXAMPLE 2a)

(Comparative Experiment to Example 2b) without Addition of Polyethylene Glycol)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS), corresponding to a molar ratio of rhodium to ligand of 1:100, and 21 ml of degassed distilled water and introduced under a stream of nitrogen into a 200 ml steel autoclave. The catalyst solution thus prepared is heated at 125° C. under 25 bar synthesis gas pressure (CO/H$_2$=1/1) for 3 hours while stirring, with the active catalyst complex being formed and the solution acquiring a yellow color.

II Hydroformylation 37.7 ml (240 mmol) of 1-octene are added to the preformed catalyst solution from I at a reaction pressure of 30 bar and at 125° C. via an upstream 200 ml steel autoclave using slight overpressure. The ratio of olefin to rhodium is, as previously, 1039:1. The hydroformylation reaction is started by switching on the magnetic stirrer. During a reaction time of 3 hours, the temperature is held at 125° C. and the reaction pressure is kept constant within a pressure band of ±2 bar by manual addition of synthesis gas. After 3 hours, stirrer and heating are switched off, the autoclave is cooled to from 40 to 50° C. and, after a settling time of from 30 to 60 minutes, the upper product phase is separated from the catalyst phase by means of phase separation in a separating funnel. Product phase and catalyst phase are weighed. The composition of the product phase is determined by means of gas chromatography and $^1$H-NMR spectroscopy, and the degree of conversion and the selectivity are determined from the composition. The rhodium content of the organic phase is, after digestion of the sample, determined by elemental analysis using graphite-furnace atomic absorption spectrometry. The yield of hydroformylation product is 9.1% and the n/iso ratio is 98:2. The organic phase contains <0.05 ppm of Rh. (Example 2a) in Table 2).

EXAMPLE 2b)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS) and added while stirring to 21 ml of degassed polyethylene gylcol 400 (warming!). This catalyst phase is introduced under a stream of nitrogen into a 200 ml steel autoclave and heated at 125° C. under 25 bar synthesis gas pressure ($CO/H_2=1/1$) for 3 hours.

II Hydroformylation 37.7 ml (240 mmol) of 1-octene are added as described in Example 2a) to the preformed catalyst solution from I at 30 bar and at 125° C. The hydroformylation reaction is carried out using a method similar to Example 2a). After 3 hours, stirrer and heating are switched off, the autoclave is cooled to from 40 to 50° C. and, after a settling time of from 30 to 60 minutes, the upper product phase is separated from the catalyst phase by means of phase separation in a separating funnel. Product phase and catalyst phase are weighed and the composition of the product phase is analyzed as described above. The yield of hydroformylation products (n- and iso-nonanal, traces of nonanol and pelargonic acid) is 58.9% and the ratio of n-nonanal to 2-methyloctanal is 92:8. The organic phase contains <0.5 ppm of Rh. (Example 2b) in Table 2).

EXAMPLE 2c)

(Comparative Experiment to Example 2d) without Addition of a Compound of the Formula (1))

The procedure of Example 2a) is repeated, but a reaction pressure of 50 bar is employed in the formylation reaction I. After a reaction time of 3 hours, the product phase is separated off and analyzed as described above. The yield of hydroformylation products is 7.6% and the n/iso ratio is 95:5. The organic phase contains <0.03 ppm of Rh. (Example 2c) in Table 2).

EXAMPLE 2d)

The procedure of Example 2b) is repeated, but a reaction pressure of 50 bar is employed in the hydroformylation reaction. After a reaction time of 3 hours, the product phase is separated off and analyzed as described above. The yield of hydroformylation products is 78.9% and the n/iso ratio is 90:10. The organic phase contains 0.2 ppm of Rh. (Example 2d) in Table 2).

EXAMPLE 2e)

(Comparative Experiment to Example 2f) without Addition of Polyethylene Glycol)

The procedure of Example 2a) is repeated, i.e. the composition of the catalyst phase and the preformation conditions are identical. However, a reaction pressure of 80 bar is employed in the hydroformylation reaction. After a reaction time of 3 hours, the product phase is separated off and analyzed as described above. The yield of hydroformylation products is 7.9% and the n/iso ratio is 95:5. The organic phase contains <0.5 ppm of Rh. (Example 2e) in Table 2).

EXAMPLE 2f)

The procedure of Example 2b) is repeated, i.e. the catalyst phase is composed of 60 mg of rhodium(III) acetate, 39 ml of a 0.6 M aqueous solution of trisodium tri(m-sulfophenyl) phosphine and 21 ml of degassed polyethylene glycol 400. The preformation conditions are identical. However, a reaction pressure of 80 bar is employed in the hydroformylation reaction. After a reaction time of 3 hours, the product phase is separated off and analyzed as described above. The yield of hydroformylation products is 76.2% and the n/iso ratio is 85:15. The organic phase contains 0.04 ppm of Rh. (Example 2f) in Table 2).

EXAMPLES 2g) to s)

The further examples (Example 2g) to 2s)) of the two-phase hydroformylation of 1-octene (see also Table 2) are carried out in a similar manner. The amounts specified in Table 2 of polyethylene glycol 400, triethylene glycol, an alcohol ethoxylate (M 350, 450 PR) or Brij 35® ($C_{12}H_{25}(OCH_2CH_2)_{23}OH$) is added to a solution of 60 mg of rhodium(III) acetate in 39 ml of a 0.6 M aqueous solution of trisodium tri(m-sulfophenyl)phosphine (Na-TPPTS). If the volume of the catalyst solution is less than 60 ml, the solution is made up to a total volume of 60 ml with degassed, distilled water. The catalyst solution is preformed using a method similar to Example 2a). After addition of 37.7 ml of 1-octene, the hydroformylation reactions are carried out at the reaction pressures indicated. The yields of hydroformylation products and the rhodium content of the organic phase are summarized in Table 2.

EXAMPLE 2l)

(Comparative Experiment Similar to Example 78 of DE 31 35 127 But Using Na-TPPTS in Place of Sodium Triphenylphosphinemonosulfonate ($3-Ph_2PC_6H_5SO_3Na$) (Na-TPPMS) and Using 1-octene in Place of 1-dodecene Example 2l) is carried out using a similar method to Example 78 of DE 31 35 127, i.e. using the same ratios of starting materials, but using 1-octene as olefin. After preformation of the catalyst phase comprising 46 mg of rhodium(III) acetate, 1.04 g of Brij 35® ($C_{12}H_{25}(OCH_2CH_2)_{23}OH$), corresponding to a ratio of additive to rhodium of 5:1, 0.87 ml of a 0.6 M solution of trisodium tri(m-sulfophenyl)phosphine (Na-TPPTS), corresponding to a ratio of TPPTS to rhodium of 3:1, and 60 ml of buffer solution pH=10 ($KHCO_3$—KOH), 21.2 ml (135 mmol) of 1-octene were introduced in the usual manner and hydroformylation was carried out at a reaction pressure of 50 bar. Cooling the reaction mass to 25° C. gives a brown, strongly foaming, turbid reaction solution which no longer separates into two phases even after prolonged standing.

Part of the organic phase can be isolated by extraction of all of the yellowish reaction mass with 20 ml of pentane. The degree of conversion determined by gas-chromatographic analysis is 22.8%. (Example 2l) in Table 2).

EXAMPLE 2m)

(Comparative Experiment Using Brij 35® in Place of PEG 400)

EXAMPLE 2l) is repeated, but a catalyst solution is now made up from 46 mg of rhodium(III) acetate, 30.0 g of Brij 35® and 29 ml of a 0.6 M solution of trisodium tri(m-sulfophenyl)phosphine (Na-TPPTS), corresponding to a ratio of TPPTS to rhodium of 100:1, and preformed. Subsequently, 21.2 ml (135 mmol) of 1-octene are introduced in the usual manner and the hydroformylation is carried out at a pressure of 50 bar. This hydroformylation batch gives, after cooling, a lemon yellow paste which displays no phase separation. Extraction with pentane is not successful. (Example 2m) in Table 2).

Examples 2l) and 2m) show that Brij 35® in combination with TPPTS is not suitable for the two-phase hydroformylation, since phase separation of the original aqueous phase and the organic phase does not take place after the hydroformylation reaction.

EXAMPLE 2k)

Example 2m) is repeated, but the 30 g of Brij 35® is replaced by the same amount of PEG 400. In contrast to 2m), phase separation takes place in the case of this hydroformylation batch. After separating off the organic phase, the yield of hydroformylation products is determined by gas chromatography. It is 90.2%. The n/iso ratio is 82:18. (Example 2k) in Table 2).

EXAMPLE 2p)

Comparative Experiment Using a Mixed Polyalkylene Glycol of the Formula $CH_3[(OCH_2CH_2)_4(OCH_2CHCH_3)]_5OH$ (Trade Designation M 41/40 of Hoechst, MW About 1000)

Example 2b) is repeated, but the 21 ml of PEG 400 is replaced by the same amount of the polyalkylene glycol $CH_3[(OCH_2CH_2)_4(OCH_2CHCH_3)]_5OH$ (commercial product of Hoechst AG; designation M 41/40, molecular weight about 1000 g/mol). After separating off the organic phase, the yield of hydroformylation products is determined by gas chromatography. It is 23.0%. The n/iso ratio is 82:8 (Example 2p) in Table 2). Example 2p) demonstrates that mixed glycols having a proportion of propylene glycol units of 20% give poorer results than the pure polyethylene glycols.

3. Series Example for the Two-phase Hydroformylation of 1-octene

EXAMPLES 3a) to 3i)

(Reuse of the Aqueous Catalyst Phase)

A series of examples was carried out on the two-phase hydroformylation of 1-octene, in which the catalyst phase was used a total of 8 times in order to demonstrate that catalyst phase can be reused without impairment of the catalytic activity. The first example of the series was carried out using a method similar to Example 2f). After a hydroformylation time of 3 hours, the autoclave was cooled to 50° C. and the upper organic phase was transferred from the autoclave into a receiver autoclave by means of a riser pipe which dips into the hydroformylation product and ends above the phase boundary, using slight overpressure. Examples 3b) to 3i) were each carried out using the catalyst phase from the previous example, by in each case adding 37.7 ml of 1-octene to the catalyst phase in the usual manner, carrying out the hyroformylation reaction and separating off the organic phase as described above.

The reaction conditions, the yields achieved, the n/iso ratios and the rhodium content of the organic phase are summarized in Table 3.

TABLE 2

Hydroformylation of 1-octene
Constant conditions: T = 125° C., total volume of catalyst phase = 60 ml, olefin/Rh ratio as indicated, amount of 1-olefin as indicated; TPPTS/Rh ratio as indicated; amount of Rh(III)ac$_3$ as indicated

| Example | i-Octene [mmol] | Rh [mmol] | Octene:Rh | P:Rh | Additive Type | Amount [ml] | % by weight[1] | Pressure [bar] | t[min] | Yield [%] | n/iso[2] | Rh[ppm][3] |
|---------|-----------------|-----------|-----------|------|---------------|-------------|----------------|----------------|--------|-----------|----------|------------|
| 2a) | 240 | 0.233 | 1039 | 100:1 | — | — | — | 30 | 180 | 9.1 | 98:2 | <0.05 |
| 2b) | 240 | 0.233 | 1039 | 100:1 | PEG 400 | 21 ml | 35 | 30 | 180 | 58.9 | 92:8 | <0.5 |
| 2c) | 240 | 0.233 | 1039 | 100:1 | — | — | — | 50 | 180 | 7.6 | 95:5 | n.d. |
| 2d) | 240 | 0.233 | 1039 | 100:1 | PEG 400 | 21 ml | 35 | 50 | 180 | 78.9 | 90:10 | 0.2 |
| 2e) | 240 | 0.233 | 1039 | 100:1 | — | — | — | 80 | 180 | 7.9 | 95:5 | <0.5 |
| 2f) | 240 | 0.233 | 1039 | 100:1 | PEG 400 | 21 ml | 35 | 80 | 180 | 62.9 | 83:17 | 0.11 |
| 2g) | 240 | 0.233 | 1039 | 100:1 | PEG 400 | 30 ml | 44 | 30 | 180 | 87.5 | 82:18 | n.d. |
| 2h) | 240 | 0.233 | 1039 | 100:1 | PEG 400 | 39 ml | 50 | 30 | 180 | 80.7 | 87:13 | 0.06 |
| 2j) | 120 | 0.116 | 1039 | 100:1 | PEG 400 | 30 ml | 61 | 50 | 180 | 88.8 | 79:21 | n.d. |
| 2k) | 135 | 0.174 | 710 | 100:1 | PEG 400 | 30 g | 44 | 50 | 180 | 90.2 | 82:18 | 0.74 |
| 2l) | 135 | 0.174 | 710 | 3:1 | Brij 354 | 1.04 g | 1.6 | 50 | 180 | 22.8 | 77:23 | n.d. |
| 2m) | 135 | 0.174 | 710 | 100:1 | Brij 354 | 30.0 g | 40 | 50 | 180 | n.d. | n.d. | n.d. |
| 2n) | 240 | 0.233 | 1039 | 100:1 | M 350[5] | 21 ml | 34 | 30 | 180 | 59.2 | 91:9 | n.d. |
| 2o) | 240 | 0.233 | 1039 | 100:1 | M 350[5] | 21 ml | 34 | 50 | 180 | 63.1 | 89:11 | n.d. |
| 2p) | 240 | 0.233 | 1039 | 100:1 | M41/40[6] | 21 ml | 33 | 50 | 180 | 23.0 | 92:8 | n.d. |
| 2q) | 240 | 0.233 | 1039 | 100:1 | 450PR[7] | 21 ml | 34 | 50 | 180 | 69.0 | 88:12 | n.d. |
| 2r) | 240 | 0.233 | 1039 | 100:1 | TriEG[8] | 21 ml | 35 | 50 | 180 | 58.9 | 89:11 | n.d. |
| 2s) | 240 | 0.233 | 1039 | 100:1 | TriEG[9] | 3.3 g | 5 | 50 | 180 | 11.0 | 95:5 | n.d. |

[1]% by weight of additive based on the catalyst phase
[2]Ratio of n-nonanal to 2-methyloctanal
[3]Rhodium content of the organic phase
[4]Polyoxyethylene lauryl ether containing about 23 ethoxy units $C_{12}H_{25}(OCH_2CH_2)_{23}OH$; in both experiments, no phase separation takes place.
[5]M 350 = $CH_3(OCH_2CH_2)_nOH$; n = 5 to 9; [6]M41/40 = $CH_3[(OCH_2CH_2)_4(OCH_2CHCH_3)]_nO_H$; n = 5 to 5; [7]450PR = $CH_3CHOHCH_2(OCH_2CH_2)_nOH$; n = 8 = −14;
[9]TriEG - Triethylene glycol $H(OCH_2CH_2)_3OH$; n.d. = not determined or, in Examples 2l) and 2m) not determinable

TABLE 3

Hydroformylation of 1-octene with repeated use of the catalyst phase
Constant conditions: T = 125° C., 240 mmol of olefin, ligand:
TPPTS, total volume of catalyst phase = 60 ml, weight of rhodium(III)
acetate used = 60 mg; TPPTS/Rh ratio = 100/1; olefin/Rh ratio = 1039/1

| Example | 1-Octene [mmol] | Rh [mmol] | Additive Type | Amount [ml] | % by weight[1] | Pressure [bar] | t[min] | Yield [%] | n/iso[2] | Rh[ppm][3] |
|---|---|---|---|---|---|---|---|---|---|---|
| 3a) | 240 | 0.233 | PEG 400 | 21 | 35 | 80 | 180 | 65.74 | 85:15 | <0.03 |
| 3b) | 240 | 0.233 | PEG 400 | 21 | 35 | 80 | 180 | 63.3 | 86:14 | 0.08 |
| 3c) | 240 | 0.233 | PEG 400 | 21 | 35 | 80 | 180 | 61.3 | 86:14 | 0.07 |
| 3e) | 240 | 0.233 | PEG 400 | 21 | 35 | 80 | 180 | 63.0 | 86:14 | 0.05 |
| 3f) | 240 | 0.233 | PEG 400 | 21 | 35 | 80 | 180 | 69.5 | 85:15 | 0.04 |
| 3g) | 240 | 0.233 | PEG 400 | 21 | 35 | 80 | 180 | 61.5 | 86:14 | 0.04 |
| 3h) | 240 | 0.233 | PEG 400 | 21 | 35 | 80 | 180 | 76.2 | 85:15 | 0.04 |
| 3i) | 240 | 0.233 | PEG 400 | 21 | 35 | 80 | 180 | 54.1 | 89:11 | 0.04 |

[1]% by weight of additive based on the catalyst phase
[2]Ratio of n-nonanal to 2-methyloctanal (iso-nonanal)
[3]Rhodium content of the organic phase

4. Hydroformylation of 4-vinylcyclohexene

EXAMPLE 4a)
(Comparative Experiment to Examples 4b) and 4c) without Addition of Polyethylene Glycol)

I Preparation of the Catalyst Phase and Preformation

The catalyst phase is prepared and preformed using a method similar to Example 1a).

II Hydroformylation 31.3 ml (240 mmol) of 4-vinylcyclohexene are added, as described above, to the preformed catalyst solution and the hydroformylation reaction is carried out at a reaction pressure of 80 bar and at 125° C. After phase separation, the product phase is analyzed in the usual manner. The yield of hydroformylation product is 60.8% and the n/iso ratio is 97:3. The organic phase contains 0.03 ppm of Rh. (Example 4a) in Table 4).

EXAMPLE 4b)

The catalyst phase is made from 60 mg of rhodium(III) acetate, 39 ml of a 0.6 M solution of trisodium tri(m-sulfophenyl)phosphine (Na-TPPTS), 11 ml of degassed polyethylene glycol 400 and 10 ml of degassed water and is preformed as described above. 31.3 ml of 4-vinylcyclohexene (240 mmol) are added as described above to the preformed catalyst solution and the hydroformylation reaction is carried out at a reaction pressure of 80 bar and at 125° C. The reaction is complete after only 150 minutes. After phase separation, the product phase is analyzed. The yield of hydroformylation product is 96.7% and the nriso ratio is 94:6. The organic phase contains 0.19 ppm of Rh. (Example 4b) in Table 4).

EXAMPLE 4c)

The catalyst phase is made up from 60 mg of rhodium(III) acetate, 39 ml of a 0.6 M solution of trisodium tri(m-sulfophenyl)phosphine (Na-TPPTS), 5 ml of degassed polyethylene glycol 400 and 16 ml of degassed water and is preformed as described above. 31.3 ml of 4-vinylcyclohexene (240 mmol) are added as described above to the preformed catalyst solution and the hydroformylation reaction is carried out at a reaction pressure of 80 bar and at 125° C. The reaction is complete after only 2.5 hours, the phase separation is carried out and the product phase is analyzed as usual. The yield of hydroformylation product is 92.3% and the n/iso ratio is 95:5. The organic phase contains 0.15 ppm of Rh. (Example 4c) in Table 4).

EXAMPLE 4d)

Example 4c) is repeated, except that a pressure of 50 bar is employed in the hydroformylation reaction and the reaction time is increased to 3 hours. The yield of hydroformylation product is 87.6% and the n/iso ratio is 97:3. The organic phase contains 0.03 ppm of Rh. (Example 4d) in Table 4).

EXAMPLE 4e)
(Comparative Experiment to Examples 4d) and 4f) without Addition of Polyethylene Glycol)

The catalyst phase is made up and preformed using a method similar to Example 4a). 31.3 ml (240 mmol) of 4-vinylcyclohexene are added as described above to the preformed catalyst solution and the hydroformylation reaction is carried out at a reaction pressure of 50 bar and at 125° C. The hydroformylation reaction is not complete until 500 minutes have elapsed, the phase separation is carried out and the product phase is analyzed as usual. The yield of hydroformylation product is 82.5% and the n/iso ratio is 98:2. The organic phase contains 0.04 ppm of Rh. (Example 4e) in Table 4).

EXAMPLE 4f)

The catalyst phase is made up and preformed using a method similar to Example 4c). 31.3 ml (240 mmol) of 4-vinylcyclohexene are added as described above to the preformed catalyst solution and the hydroformylation reaction is carried out at a reaction pressure of 50 bar and at 125° C. The reaction is complete after 4 hours, the phase separation is carried out and the product phase is analyzed as usual. The yield of hydroformylation product is 95.8% and the n/iso ratio is 97:3. The organic phase contains <0.03 ppm of Rh. (Example 4f) in Table 4). The reaction conditions and the analytical data for Examples 4a) to 4f) are summarized in Table 4 below.

TABLE 4

Hydroformylation of 4-vinylcyclohexene
Constant conditions: T = 125° C., 240 mmol of olefin, weight of rhodium(III) acetate used = 60 mg;
TPPTS/Rh ratio = 100:1; olefin/Rh ratio = 1039:1

| Example | Olefin [ml] | Rh cat. [mmol] | Olefin:Rh | Additive Type | Additive [ml] | % by weight[1] | P[bar] | t[min] | Yield [%] | n/iso[2] | Rh[ppm][3] |
|---|---|---|---|---|---|---|---|---|---|---|---|
| 4a) | 31.3 | 0.233 | 1039 | — | — | — | 80 | 180 | 60.8 | 97:3 | 0.03 |
| 4b) | 31.3 | 0.233 | 1039 | PEG 400 | 11 | 19 | 80 | 120 | 96.7 | 94:6 | 0.19 |
| 4c) | 31.3 | 0.233 | 1039 | PEG 400 | 5 | 9 | 80 | 150 | 92.3 | 95:5 | 0.15 |
| 4d) | 31.3 | 0.233 | 1039 | PEG 400 | 5 | 9 | 50 | 180 | 87.6 | 97:3 | 0.03 |
| 4e) | 31.3 | 0.233 | 1039 | — | — | — | 50 | 492 | 82.5 | 98:2 | 0.04 |
| 4f) | 31.3 | 0.233 | 1039 | PEG 400 | 5 | 9 | 50 | 240 | 95.8 | 97:3 | <0.03 |

[1]% by weight of additive based on the catalyst phase
[2]Ratio of 3-(cyclohexenyl)propanal to branched aldehydes
[3]Rhodium content of the organic phase

5. Hydroformylation of 1-decene

EXAMPLE 5a)
(Comparative Experiment to Example 5b) without Addition of Polyethylene Glycol)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPS), corresponding to a molar ratio of rhodium to ligand of 1:100, and 21 ml of degassed distilled water and introduced under a stream of nitrogen into a 200 ml steel autoclave. The catalyst solution thus prepared is heated at 125° C. under 25 bar synthesis gas pressure ($CO/H_2=1/1$) for 3 hours, with the active catalyst complex being formed and the solution becoming intense yellow.

II Hydroformylation 45.5 ml (240 mmol) of 1-decene are added to the preformed catalyst solution under a reaction pressure of 30 bar and at 125° C. via an upstream 200 ml steel autoclave, by using slight overpressure. The ratio of olefin to rhodium is 1039:1. The hydroformylation reaction is carried out similarly to the preceding examples at 30 bar synthesis gas pressure. After 3 hours, stirrer and heating are switched off, the autoclave is cooled to from 40 to 50° C. and the upper product phase is separated from the catalyst phase by means of phase separation in a separating funnel. Product phase and catalyst phase are weighed. The composition of the product phase is analyzed as described above. The yield of hydroformylation product is 1.9% and the n/iso ratio is 100:0. The organic phase contains <0.03 ppm of Rh. (Example 5a) in Table 5).

EXAMPLE 5b)

The catalyst phase is made up and preformed using a method similar to Example 1b). 95.5 ml (240 mmol) of 1-decene are added as described above to the preformed catalyst solution and the hydroformylation reaction is carried out at a reaction pressure of 30 bar and at 125° C. After phase separation, the product phase is analyzed.

The yield of hydroformylation product is 19.1% and the n/iso ratio is 93:7. The organic phase contains <0.03 ppm of Rh. (Example 5b) in Table 5).

EXAMPLE 5c)
(Comparative Experiment to Example 5d) without Addition of Polyethylene Glycol)

The procedure of Example 5a) is repeated, except that a reaction pressure of 80 bar is employed in the hydroformylation reaction. After a reaction time of 3 hours, the product phase is separated off and analyzed as described above. The yield of hydroformylation products is 2.7% and the n/iso ratio is 94:6. The organic phase contains <0.03 ppm of Rh. (Example 5c) in Table 5).

EXAMPLE 5d)

The procedure of Example 5b) is repeated, except that the hydroformylation reaction is carried out at a pressure of 80 bar. After a reaction time of 3 hours, the product phase is separated off and analyzed as described above. The yield of hydroformylation products is 43.0% and the n/iso ratio is 87:13. The organic phase contains 0.26 ppm of Rh. (Example 5d) in Table 5).

The reaction conditions and the analytical data for Examples 5a) to 5d) are shown in Table 5 below.

TABLE 5

Hydroformylation of 1-decene
Constant conditions: T = 125° C., 240 mmol of olefin,
Weight of rhodium(III) acetate used = 60 mg; TPPTS/Rh ratio = 100: 1; olefin/Rh ratio = 1039: 1

| Example | 1-Decene [mmol] | Rh cat. [mmol] | Olefin:Rh | Additive Type | Additive [ml] | % by weight of additive[1] | P[bar] | t[min] | Yield [%] | n/iso[2] | Rh [ppm][3] |
|---|---|---|---|---|---|---|---|---|---|---|---|
| 5a) | 240 | 0.233 | 1039 | — | — | — | 30 | 180 | 1.9 | 100:0 | <0.03 |
| 5b) | 240 | 0.233 | 1039 | PEG 400 | 21 | 35 | 30 | 180 | 19.1 | 93:7 | <0.03 |
| 5c) | 240 | 0.233 | 1039 | — | — | — | 80 | 180 | 2.7 | 94:6 | <0.03 |

TABLE 5-continued

Hydroformylation of 1-decene
Constant conditions: T = 125° C., 240 mmol of olefin,
Weight of rhodium(III) acetate used = 60 mg; TPPTS/Rh ratio = 100: 1; olefin/Rh ratio = 1039: 1

| Example | 1-Decene [mmol] | Rh cat. [mmol] | Olefin:Rh | Additive Type | Additive [ml] | % by weight of additive[1] | P[bar] | t[min] | Yield [%] | n/iso[2] | Rh [ppm][3] |
|---|---|---|---|---|---|---|---|---|---|---|---|
| 5d) | 240 | 0.233 | 1039 | PEG 400 | 21 | 35 | 80 | 180 | 43 | 87:13 | 0.26 |

[1]% by weight of additive based on the catalyst phase
[2]Ratio of n-undecanal to 2-methyldecanal (iso-decanal)
[3]Rhodium content to the organic phase 6. Hydroformylation of 1-dodecene

EXAMPLE 6a)

(Comparative Experiment to Example 6b) without Addition of Polyethylene Glycol)

The catalyst phase is prepared and preformed using a method similar to Example 1a). 53.3 ml (240 mmol) of 1-dodecene are added as described above to the preformed catalyst solution and the hydroformylation reaction is carried out for 3 hours at a reaction pressure of 30 bar and at 125° C. After phase separation, the product phase is analyzed. The yield of hydroformylation product is 0%. The organic phase contains <0.03 ppm of Rh. (Example 6a) in Table 6).

EXAMPLE 6b)

The catalyst is made up in a similar way to 1b) and is preformed as described above. 53.3 ml (240 mmol) of 1-dodecene are added as described above to the preformed catalyst solution and the hydroformylation reaction is carried out for 3 hours at a reaction pressure of 30 bar and at 125° C. After phase separation, the product phase is analyzed. The yield of hydroformylation product is 9.2% and the n/iso ratio is 87:13. The organic phase contains <0.5 ppm of Rh. (Example 6b) in Table 6).

EXAMPLE 6c)

(Comparative Experiment to Example 6d) without Addition of Polyethylene Glycol)

The catalyst phase is prepared and preformed using a method similar to Example 1a). 53.3 ml (240 mmol) of 1-dodecene are added as described above to the preformed catalyst solution and the hydroformylation reaction is carried out for 3 hours at a reaction pressure of 80 bar and at 125° C. After phase separation, the product phase is analyzed. The yield of hydroformylation product is <1%. Owing to the low yield, the n/iso ratio cannot be determined. The organic phase contains <0.5 ppm of Rh. (Example 6c) in Table 6).

EXAMPLE 6d)

The catalyst phase is made up in a similar way to 1b) and is preformed as described above. 53.3 ml (240 mmol) of 1-dodecene are added as described above to the preformed catalyst solution and the hydroformylation reaction is carried out for 3 hours at a reaction pressure of 80 bar and at 125° C. After phase separation, the product phase is analyzed.

The yield of hydroformylation product is 13.0% and the n/iso ratio is 75:25. The organic phase contains 0.03 ppm of Rh. (Example 6d) in Table 6).

EXAMPLE 6e)

The catalyst phase is made up from 60 mg of rhodium(III) acetate, 21 ml of a 0.6 M aqueous solution of trisodium tri(m-sulfophenyl)phosphine (Na-TPPTS) and 39 ml of PEG 400 and is preformed. Here, the ratio of TPPTS to rhodium is 54:1. The hydroformylation reaction is carried out for 3 hours at a reaction pressure of 80 bar and at 125° C. After phase separation, the product phase is analyzed. The yield of hydroformylation product is 76.4% and the n/iso ratio is 72:28. The organic phase contains 0.52 ppm of Rh. (Example 6e) in Table 6).

EXAMPLE 6f)

The catalyst phase is made up from 60 mg of rhodium(III) acetate, 15.5 ml of a 0.6 M aqueous solution of trisodium tri(m-sulfophenyl)phosphine (Na-TPPTS) (9.32 mmol) and 40 ml of PEG 400 and is preformed. Here, the ratio of TPPTS to rhodium is 40:1. The hydroformylation reaction is carried out for 3 hours at a reaction pressure of 50 bar and at 125° C. After phase separation, the product phase is analyzed. The yield of hydroformylation product is 59.0% and the n/iso ratio is 76:24. The organic phase contains 0.08 ppm of Rh. (Example 6f) in Table 6). The reaction conditions and the analytical data for Examples 6a) to 6f) are shown in Table 6 below.

TABLE 5

Hydroformylation of 1-dodecene
Constant conditions: T = 125° C., 240 mmol of olefin,
Weight of rhodium(III) acetate used = 60 mg; TPPTS/Rh ratio as indicated; olefin/Rh ratio = 1039 : 1

| Example | 1-Decene [mmol] | Rh cat. [mmol] | Additive Type | Additive [ml] | % by weight of additive[1] | P:Rh | P[bar] | t[min] | Yield [%] | n/iso[2] | Rh[ppm][3] |
|---|---|---|---|---|---|---|---|---|---|---|---|
| 6a) | 240 | 0.233 | — | — | — | 100:1 | 30 | 180 | 0 | n.d. | <0.05 |
| 6b) | 240 | 0.233 | PEG 400 | 21 | 35 | 100:1 | 30 | 180 | 9.2 | 87:13 | <0.5 |
| 6c) | 240 | 0.233 | — | — | — | 100:1 | 80 | 180 | <1 | n.d. | <0.5 |
| 6d) | 240 | 0.233 | PEG 400 | 21 | 35 | 100:1 | 80 | 180 | 13 | 75:25 | 0.03 |
| 6e) | 240 | 0.233 | PEG 400 | 39 | 63 | 54:1 | 80 | 180 | 76.4 | 72:28 | 0.52 |
| 6f) | 240 | 0.233 | PEG 400 | 40 | 70 | 40:1 | 50 | 180 | 59 | 76:24 | 0.08 |

[1] % by weight of additive based on the catalyst phase
[2] Ratio of n-tridecanal to 2-methyldodecanal (iso-tridecanal)
[3] Rhodium content of the organic phase

What is claimed is:

1. A process for preparing aldehydes, which comprises reacting an olefinically unsaturated compound having from 6 to 16 carbon atoms with hydrogen and carbon monoxide at from 20 to 170° C. and from 1 to 300 bar in the presence of an aqueous phase comprising rhodium and sulfonated triarylphosphines as catalyst and from 10 to 70% by weight of a compound of the formula (1) $R(OCH_2CH_2)_nOR^1$, where, in the formula (1), R is hydrogen, a straight-chain or branched alkyl radical having from 1 to 4 carbon atoms or a hydroxyalkyl radical having from 1 to 4 carbon atoms, $R^1$ is hydrogen or a methyl radical and n is an integer from 3 to 50.

2. The process as claimed in claim 1, wherein the olefinically unsaturated compound used is an aliphatic olefin, cycloaliphatic olefin or araliphatic olefin having from 6 to 16 carbon atoms.

3. The process as claimed in claim 1, wherein the olefinic compound used is an aliphatic or cycloaliphatic α-olefin having from 6 to 12 carbon atoms.

4. The process as claimed in claim 1, wherein the trisulfonated triarylphosphines used are compounds of the formula (2)

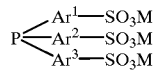

where $Ar^1$, $Ar^2$ and $Ar^3$ are identical or different and are each a phenyl or naphthyl radical and M are identical or different and are each an alkali metal ion, an ammonium ion, a quaternary ammonium ion or a ½ alkaline earth metal ion or ½ zinc ion.

5. The process as claimed in claim 1, wherein the sulfonated triarylphosphine used is a sulfonated triphenylphosphine.

6. The process as claimed in claim 1, wherein the sulfonated triarylphosphine used is trisodium tri(m-sulfophenyl)phosphine.

7. The process as claimed in claim 1, wherein the aqueous phase is used in an amount corresponding to from $2\times10^{-6}$ to $5\times10^{-2}$ mol of rhodium per mol of olefinic compound.

8. The process as claimed in claim 4, wherein rhodium and sulfonated triarylphosphines of the formula (2) are used in a molar ratio of from 1:10 to 1:1000.

9. The process as claimed in claim 4, wherein rhodium and sulfonated triarylphosphines of the formula (2) are used in a molar ratio of from 1:50 to 1:200.

10. The process as claimed in claim 4, wherein the aqueous phase contains from 100 to 1000 ppm of rhodium when using sulfonated triarylphosphines of the formula (2).

11. The process as claimed in claim 4, wherein the aqueous phase contains from 200 to 500 ppm of rhodium when using sulfonated triarylphosphines of the formula (2).

12. The process as claimed in claim 4, wherein the aqueous phase contains from 300 to 400 ppm of rhodium when using sulfonated triarylphosphines of the formula (2).

13. The process as claimed in claim 1, wherein the sulfonated triarylphosphines used are compounds of the formula (3)

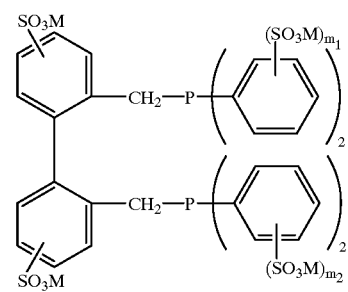

where $m_1$ and $m_2$ are, independently of one another, 0 or 1 and the compounds of the formula (3) contain from three to six $—SO_3M$ groups, where M is as defined in claim 1.

14. The process as claimed in claim 1, wherein the sulfonated triarylphosphines used are compounds of the formula (4)

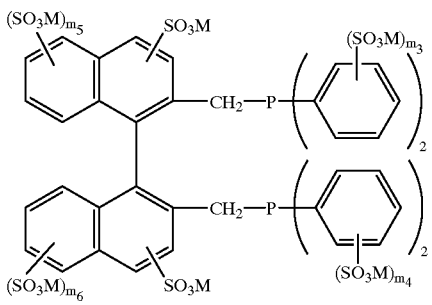

(4)

where $m_3$, $m_4$, $m_5$ and $m_6$ are, independently of one another, 0 or 1 and the compounds of the formula (4) have from four to eight —$SO_3M$ groups, where M is as defined in claim 1.

15. The process as claimed in claim 13, wherein rhodium and sulfonated triarylphosphines of the formula (3) are used in a molar ratio of 1:5 to 1:100.

16. The process as claimed in claim 13, wherein rhodium and sulfonated triarylphosphines of the formula (3) are used in a molar ratio of 1:5 to 1:50.

17. The process as claimed in claim 13, wherein rhodium and sulfonated triarylphosphines of the formula (3) are used in a molar ratio of 1:8 to 1:15.

18. The process as claimed in claim 13, wherein the aqueous phase contains from 20 to 500 ppm of rhodium when using sulfonated triarylphosphines of the formula (3).

19. The process as claimed in claim 13, wherein the aqueous phase contains from 30 to 150 ppm of rhodium when using sulfonated triarylphosphines of the formula (3).

20. The process as claimed in claim 13, wherein the aqueous phase contains from 40 to 100 ppm of rhodium when using sulfonated triarylphosphines of the formula (3).

21. The process as claimed in claim 1, wherein an aliphatic α-olefin or cycloaliphatic olefin having from 6 to 8 carbon atoms is reacted in the presence of an aqueous phase containing from 10 to 50% by weight of the compound of the formula (1).

22. The process as claimed in claim 1, wherein an aliphatic α-olefin or a cycloaliphatic olefin having from 6 to 8 carbon atoms is reacted in the presence of an aqueous phase containing from 20 to 40% by weight of the compound of the formula (1).

23. The process as claimed in claim 1, wherein an aliphatic α-olefin or cycloaliphatic olefin having from 9 to 12 carbon atoms is reacted in the presence of an aqueous phase containing from 30 to 70% by weight of the compound of the formula (1).

24. The process as claimed in claim 1, wherein an aliphatic α-olefin or cycloaliphatic olefin having from 9 to 12 carbon atoms is reacted in the presence of an aqueous phase containing from 50 to 60% by weight of the compound of the formula (1).

25. The process as claimed in claim 1, wherein the compound of the formula (1) used is a polyethylene glycol of the formula $H(OCH_2CH_2)_nOH$, where n is an integer from 3 to 50.

26. The process as claimed in claim 1, wherein the compound of the formula (1) used is a polyethylene glycol of the formula $H(OCH_2CH_2)_nOH$, where n is an integer from 4 to 30.

27. The process as claimed in claim 1, wherein the compound of the formula (1) used is a compound of the formula $R(OCH_2CH_2)_nOH$, where R is a methyl radical or β-hydroxypropyl radical and n is an integer from 3 to 50.

28. The process as claimed in claim 1, wherein the compound of the formula (1) used is a compound of the formula $R(OCH_2CH_2)_nOH$, where R is a methyl radical or β-hydroxypropyl radical and n is an integer from 4 to 30.

29. The process as claimed in claim 1, wherein the reaction is carried out at from 50 to 150° C.

30. The process as claimed in claim 1, wherein the reaction is carried out at from 100 to 140° C.

31. The process as claimed in claim 1, wherein the reaction is carried out at from 20 to 150 bar.

32. The process as claimed in claim 1, wherein the reaction is carried out at from 30 to 80 bar.

33. The process as claimed in claim 14 wherein rhodium and sulfonated triarylphosphines of the formula (4) are used in a molar ratio of 1:5 to 1:100.

34. The process as claimed in claim 14 wherein rhodium and sulfonated triarylphosphines of the formula (4) are used in a molar ratio of 1:5 to 1:50.

35. The process as claimed in claim 14 wherein rhodium and sulfonated triarylphosphines of the formula (4) are used in a molar ratio of 1:8 to 1:15.

36. The process as claimed in claim 14 wherein the aqueous phase contains from 20 to 500 ppm of rhodium when using sulfonated triarylphosphines of the formula (4).

37. The process as claimed in claim 14 wherein the aqueous phase contains from 30 to 150 ppm of rhodium when using sulfonated triarylphosphines of the formula (4).

38. The process as claimed in claim 14 wherein the aqueous phase contains from 40 to 100 ppm of rhodium when using sulfonated triarylphosphines of the formula (4).

* * * * *